(12) United States Patent
Pollock et al.

(10) Patent No.: US 9,588,082 B2
(45) Date of Patent: Mar. 7, 2017

(54) STEAM GENERATOR TUBE PROBE AND METHOD OF INSPECTION

(71) Applicant: NuScale Power, LLC, Corvallis, OR (US)

(72) Inventors: Weston Pollock, Burke, VA (US);
Adam Rasmussen, Corvallis, OR (US);
Cristhian Galvez, Corvallis, OR (US);
Eric Paul Young, Corvallis, OR (US);
Jeff Siegel, Corvallis, OR (US)

(73) Assignee: Nuscale Power, LLC, Corvallis, OR (US)

( * ) Notice: Subject to any disclaimer, the term of this patent is extended or adjusted under 35 U.S.C. 154(b) by 357 days.

(21) Appl. No.: 14/288,556

(22) Filed: May 28, 2014

(65) Prior Publication Data

US 2014/0354273 A1 Dec. 4, 2014

Related U.S. Application Data

(60) Provisional application No. 61/829,738, filed on May 31, 2013.

(51) Int. Cl.
*G01N 27/90* (2006.01)
*F22B 37/00* (2006.01)
*F22B 1/16* (2006.01)

(52) U.S. Cl.
CPC .......... *G01N 27/902* (2013.01); *F22B 1/162* (2013.01); *F22B 37/003* (2013.01)

(58) Field of Classification Search
CPC ...... F22B 1/162; F22B 37/003; F22B 37/002; G01N 27/902; G21C 17/017

USPC .................................................. 324/220–221
See application file for complete search history.

(56) References Cited

U.S. PATENT DOCUMENTS

| | | | | |
|---|---|---|---|---|
| 3,105,548 A | * | 10/1963 | Ownby | E21B 23/02 166/123 |
| 3,786,684 A | * | 1/1974 | Wiers | G01M 3/005 324/220 |
| 3,906,358 A | * | 9/1975 | Stone | F22B 37/003 324/220 |
| 4,668,912 A | | 5/1987 | Junker | |
| 4,673,027 A | | 6/1987 | Vermaat | |

(Continued)

FOREIGN PATENT DOCUMENTS

| | | | |
|---|---|---|---|
| CN | 102903407 | * | 1/2013 |
| JP | 9505526 T | | 6/1997 |

(Continued)

OTHER PUBLICATIONS

English translation of Korean Patent KR101160662.*

(Continued)

*Primary Examiner* — Jay Patidar
(74) *Attorney, Agent, or Firm* — Lowe Graham Jones, PLLC (57) ABSTRACT

A steam generator tube probe includes a probe head comprising an electronic probe coupled between a proximal portion of the head that is configured for entry into a steam generator tube and a distal portion of the head; and a probe shaft coupled to the distal portion of the shaft and comprising a flexible metallic conduit that comprises a plurality of interlocking portions, each interlocking portion moveably affixed to at least one adjacent interlocking portion.

8 Claims, 9 Drawing Sheets

(56) References Cited

U.S. PATENT DOCUMENTS

| | | | |
|---|---|---|---|
| 4,704,577 A | 11/1987 | Junker | |
| 4,763,274 A | 8/1988 | Junker | |
| 4,814,702 A | 3/1989 | Driggers | |
| 4,855,677 A | 8/1989 | Clark | |
| 4,937,524 A | 6/1990 | Fasnacht | |
| 4,952,875 A * | 8/1990 | Adams | G21C 17/017 324/220 |
| 5,017,761 A | 5/1991 | Brunner | |
| 5,023,549 A * | 6/1991 | Dau | G01N 27/9033 324/220 |
| 5,068,608 A | 11/1991 | Clark | |
| 5,134,367 A | 7/1992 | Griffith | |
| 5,256,966 A | 10/1993 | Edwards | |
| 5,408,883 A | 4/1995 | Clark | |
| 5,606,792 A | 3/1997 | Schafer | |
| 5,667,252 A | 9/1997 | Schafer | |
| 5,767,410 A | 6/1998 | Lareau | |
| 5,791,046 A | 8/1998 | Schafer | |
| 5,836,199 A * | 11/1998 | Loud | F22B 37/002 59/78.1 |
| 6,145,583 A | 11/2000 | Gay et al. | |
| 6,388,439 B1 * | 5/2002 | Lembeye | G01N 27/902 324/207.16 |
| 6,429,649 B1 * | 8/2002 | Boynton | G01N 27/902 324/220 |
| 6,519,535 B1 | 2/2003 | Petri | |
| 6,556,012 B2 | 4/2003 | Yamashita | |
| 6,677,748 B2 | 1/2004 | Hur | |
| 6,823,269 B2 | 11/2004 | Junker | |
| 6,923,078 B2 | 8/2005 | Loud | |
| 7,071,693 B2 | 7/2006 | Yasuhara | |
| 7,112,963 B2 | 9/2006 | Hasegawa | |
| 7,188,501 B2 | 3/2007 | Tsuyuguchi | |
| 7,197,906 B2 | 4/2007 | Tsuyuguchi | |
| 7,242,201 B2 | 7/2007 | Lee | |
| 7,245,126 B1 | 7/2007 | Hasegawa | |
| 7,405,558 B2 | 7/2008 | Wyatt | |
| 7,528,599 B2 | 5/2009 | Zimmerman | |
| 7,570,053 B2 | 8/2009 | Hasegawa | |
| 7,587,942 B2 | 9/2009 | Smith et al. | |
| 7,597,048 B2 * | 10/2009 | Nicholson | B08B 9/035 104/138.2 |
| 7,609,064 B2 | 10/2009 | Fukuda | |
| 7,619,414 B2 | 11/2009 | Yamamoto | |
| 7,654,122 B2 | 2/2010 | Tsuyuguchi | |
| 7,711,499 B2 | 5/2010 | Junker | |
| 7,733,084 B1 | 6/2010 | O'Dell | |
| 7,750,636 B2 | 7/2010 | Shiino | |
| 7,808,242 B2 | 10/2010 | Yamamoto | |
| 8,301,401 B2 | 10/2012 | Morrison et al. | |
| 8,390,278 B2 | 3/2013 | Petrosky | |
| 8,527,216 B2 | 9/2013 | Griffith | |
| 8,581,577 B2 | 11/2013 | Draper | |
| 8,794,083 B2 | 8/2014 | Draper | |
| 2001/0022515 A1 | 9/2001 | Yamashita | |
| 2002/0153883 A1 | 10/2002 | Hur | |
| 2003/0107376 A1 | 6/2003 | Yasuhara | |
| 2003/0195710 A1 | 10/2003 | Junker | |
| 2004/0099175 A1 * | 5/2004 | Perrot | F16L 55/28 104/138.1 |
| 2004/0112154 A1 | 6/2004 | Loud | |
| 2004/0251903 A1 | 12/2004 | Hasegawa | |
| 2006/0288750 A1 | 12/2006 | Tsuyuguchi | |
| 2006/0288751 A1 | 12/2006 | Tsuyuguchi | |
| 2007/0018661 A1 | 1/2007 | Lee | |
| 2007/0194789 A1 | 8/2007 | Hasegawa | |
| 2008/0007257 A1 | 1/2008 | Wyatt | |
| 2008/0061786 A1 | 3/2008 | Fukuda | |
| 2008/0111548 A1 | 5/2008 | Yamamoto | |
| 2008/0150527 A1 | 6/2008 | Hasegawa | |
| 2008/0204015 A1 | 8/2008 | Shiino | |
| 2008/0231277 A1 | 9/2008 | Yamamoto | |
| 2008/0278157 A1 | 11/2008 | Zimmerman | |
| 2009/0054242 A1 | 2/2009 | Takahashi | |
| 2009/0064752 A1 | 3/2009 | Tsuyuguchi | |
| 2009/0121718 A1 | 5/2009 | Yamamoto | |
| 2009/0150093 A1 | 6/2009 | Junker | |
| 2011/0022333 A1 | 1/2011 | Griffith | |
| 2011/0089937 A1 | 4/2011 | Petrosky | |
| 2011/0125462 A1 | 5/2011 | Petrosky | |
| 2012/0006133 A1 * | 1/2012 | Draper | G21C 17/017 73/866.5 |
| 2012/0006134 A1 * | 1/2012 | Draper | F16L 55/30 73/866.5 |
| 2012/0007594 A1 * | 1/2012 | Draper | F22B 37/003 324/220 |
| 2013/0009634 A1 | 1/2013 | Lakhan | |
| 2013/0101153 A1 | 4/2013 | Kohashi | |
| 2013/0335111 A1 | 12/2013 | Hawkins | |
| 2013/0338940 A1 | 12/2013 | Griffith | |
| 2014/0055138 A1 | 2/2014 | Takegoshi | |
| 2014/0055139 A1 | 2/2014 | Takegoshi | |

FOREIGN PATENT DOCUMENTS

| | | | |
|---|---|---|---|
| JP | 2007071825 A | | 3/2007 |
| KR | 1160662 B1 | | 6/2012 |
| WO | WO 2006087592 | * | 8/2006 |

OTHER PUBLICATIONS

Authorized Officer Hye Lyum Park, International Search Report and Written Opinion for International Application No. PCT/US2014/039825, mailed Sep. 23, 2014, 17 pages.

Cinotti, L., et al.; Steam Generator of the International Reactor Innovative and Secure; Proceedings of ICONE10, 10th International Conference on Nuclear Engineering, Arlington, VA, Apr. 14-18, 2002; ICONE10-22570; 8 pages.

* cited by examiner

STEAM GENERATOR TUBE PROBE AND METHOD OF INSPECTION

CROSS-REFERENCE TO RELATED APPLICATION

This application claims priority under 35 U.S.C. §119 to U.S. Provisional Patent Application Ser. No. 61/829,738, entitled "INSPECTING A STEAM GENERATOR," and filed on May 31, 2013, the entire contents of which are hereby incorporated by reference.

TECHNICAL FIELD

This disclosure generally relates to inspecting and/or testing (e.g., nondestructive testing or NDT) of a tubing contained in a steam generator of a nuclear reactor system and, more particularly, an eddy current method of inspecting and/or testing steam generator tubings such as helically configured tubings.

BACKGROUND

In a nuclear reactor, a core of nuclear material is confined to a small volume internal to the reactor so that a reaction may occur. In many instances, a controlled nuclear reaction may persist for an extended period of time, such as several years, before refueling of the reactor core is required. Accordingly, when used as a source of heat for converting water into steam, a properly designed nuclear reactor may provide a carbon-free, stable, and highly reliable source of energy.

A nuclear reactor may make use of a working fluid, such as water, which may be converted to steam at a pressure significantly above atmospheric pressure. The pressurized steam may then be used to drive a turbine for converting mechanical energy to electric current. The steam may then be condensed back into water, and returned to the reactor. In many nuclear reactors, the cycle of vaporization, condensation, and vaporization of the working fluid may continue day after day and year after year. One feature of a nuclear reactor may be a steam generator that receives liquid coolant (e.g., flushed through the inner diameter (ID) of a matrix of several closely spaced thin-walled metal tubes) at an input side, vaporizes the coolant by way of exposure from the heat source of the nuclear reactor to the outer diameter (OD) of the steam generator tubes, and provides the vaporized coolant to the input of a turbine.

Steam generator tubes may sometimes need to be inspected for flaws that may compromise structural integrity of such tubes, potentially allowing the radioactive heat fluid on the OD to mix with the vaporized liquid on the ID which flows to a turbine. Such inspections are performed by inserting eddy current probes, containing a probe head with an electromagnet coil mounted on a probe shaft, through the tube bore. Such probe shafts, however, have limited flexibility and are difficult to pass through the bore of the tubes, for example when those tubes have multiple or compound tight radius bends or in regions where the tubes bend.

SUMMARY

In a general implementation, a steam generator tube probe includes a probe head comprising an electronic probe coupled between a proximal portion of the head that is configured for entry into a steam generator tube and a distal portion of the head; and a probe shaft coupled to the distal portion of the shaft and comprising a flexible metallic conduit that comprises a plurality of interlocking portions, each interlocking portion moveably affixed to at least one adjacent interlocking portion.

A first aspect combinable with the general implementation further includes a cable that extends from at or adjacent the distal end of the probe head through the probe shaft.

In a second aspect combinable with any of the previous aspects, the cable comprises a multi-strand cable.

In a third aspect combinable with any of the previous aspects, the flexible metallic conduit comprises a stainless steel square-lock conduit.

In a fourth aspect combinable with any of the previous aspects, the electronic probe comprises an eddy current test probe.

In a fifth aspect combinable with any of the previous aspects, the eddy current test probe comprises a self-referencing Bobbin coil probe.

In another general implementation, a method for testing a steam generator tube includes inserting a steam generator tube probe into an inlet of a steam generator tube, the steam generator tube probe comprising a probe head coupled to a probe shaft; circulating a gas into the steam generator tube; and urging the steam generator tube probe through at least a portion of the steam generator tube with at least a portion of the circulated gas disposed in an annulus between the probe shaft and the steam generator tube.

In a first aspect combinable with the general implementation, the steam generator tube comprises a plurality of turns.

In a second aspect combinable with any of the previous aspects, urging the steam generator tube probe through the portion of the steam generator tube comprises urging the steam generator tube probe through the plurality of turns and through an outlet of the steam generator tube.

In a third aspect combinable with any of the previous aspects, the steam generator tube comprises a helical coil steam generator tube.

A fourth aspect combinable with any of the previous aspects further includes guiding the probe head of the steam generator tube probe toward the inlet of the steam generator tube.

A fifth aspect combinable with any of the previous aspects further includes adjusting a position of the probe head in at least two directions to align the probe head with the inlet of the steam generator tube.

A sixth aspect combinable with any of the previous aspects further includes urging the aligned probe head into the inlet of the steam generator tube.

A seventh aspect combinable with any of the previous aspects further includes urging the probe head into a first inlet of a probe positioning guide assembly that is positioned adjacent the inlet of the steam generator tube.

An eighth aspect combinable with any of the previous aspects further includes circulating the gas into a second inlet of the probe positioning guide assembly.

A ninth aspect combinable with any of the previous aspects further includes urging the probe head and the gas together from an outlet of the probe positioning guide assembly and into the inlet of the steam generator tube.

A tenth aspect combinable with any of the previous aspects further includes determining a frictional resistance force on the probe shaft based on contact between the probe shaft and the steam generator tube during the urging of the steam generator tube probe through the portion of the steam generator tube.

An eleventh aspect combinable with any of the previous aspects further includes based on the determined frictional resistance force, adjusting a pressure or a flow rate of the gas circulated into the steam generator tube.

In a twelfth aspect combinable with any of the previous aspects, the gas comprises air.

In another general implementation, a steam generator tube inspection system includes an eddy current test probe that comprises: a probe head comprising an electronic probe coupled between a proximal portion of the head that is configured for entry into a steam generator tube and a distal portion of the head; and a probe shaft coupled to the distal portion of the shaft and comprising a flexible metallic conduit that comprises a plurality of interlocking portions, each interlocking portion slideably affixed to at least one adjacent interlocking portion; a probe delivery apparatus configured to convey at least a portion of the probe shaft from a spool; and an air supply that comprises a conduit to deliver a pressurized airflow to the steam generator tube.

A first aspect combinable with the general implementation further includes a cable that extends from at or adjacent the distal portion of the probe head through the probe shaft.

In a second aspect combinable with any of the previous aspects, the cable comprises a multi-strand cable.

In a third aspect combinable with any of the previous aspects, the flexible metallic conduit comprises a stainless steel square-lock conduit.

In a fourth aspect combinable with any of the previous aspects, the electronic probe comprises an eddy current test probe.

In a fifth aspect combinable with any of the previous aspects, the eddy current test probe comprises a self-referencing Bobbin coil probe.

In a sixth aspect combinable with any of the previous aspects, the probe delivery apparatus comprises a probe drive that comprises a motorized apparatus configured to convey the portion of the probe shaft from the spool; and a probe positioning drive configured to receive the portion of the probe shaft from the motorized apparatus and align the proximal portion of probe head with an inlet of the steam generator tube.

In a seventh aspect combinable with any of the previous aspects, the probe positioning drive is configured to translate the probe head in at least two directions to align the proximal portion of probe head with an inlet of the steam generator tube.

In an eighth aspect combinable with any of the previous aspects, the probe delivery apparatus further comprises a probe positioning guide assembly that comprises a first inlet portion configured to receive the probe head; a radiused portion that comprises an entry coupled to the first inlet portion; and a second inlet portion coupled to an exit of the radiused portion and configured to receive the probe head through a first opening and the pressurized airflow through a second opening.

In a ninth aspect combinable with any of the previous aspects, the second inlet portion comprises an outlet configured to provide the probe head and the pressurized airflow together to the inlet of the steam generator tube.

In another general implementation, an apparatus for testing a tubular of a nuclear reactor power system includes an eddy current electronic probe coupled to a test probe; and a bendable probe shaft coupled to the test probe, the bendable probe shaft comprising a flexible conduit that includes a plurality of telescoping joints.

In another general implementation, a method of testing a steam generator tube includes inserting a steam generator tube probe into an inlet of a helical steam generator tube, the steam generator tube probe comprising a probe head coupled to a probe shaft that includes a flexible metallic conduit comprising a plurality of interlocking portions; and urging the steam generator tube probe through at least a portion of the helical steam generator tube.

A first aspect combinable with the general implementation further includes circulating a flow of a gas through the helical steam generator tube substantially simultaneously with the urging of the steam generator tube probe through the portion of the helical steam generator tube.

Various implementations of a steam generator tube inspection probe (or steam generator probe) described in this disclosure may include none, one, some, or all of the following features. For example, the probe may permit eddy current inspection of long helically shaped tubes and tubes including multiple bends. Further, the probe may facilitate inspection of these and other steam generator tubes using a standard probe drive machine without the need for additional drive assist methods (such as hydraulic) in order to overcome probe/tube friction.

The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

Figure 1:
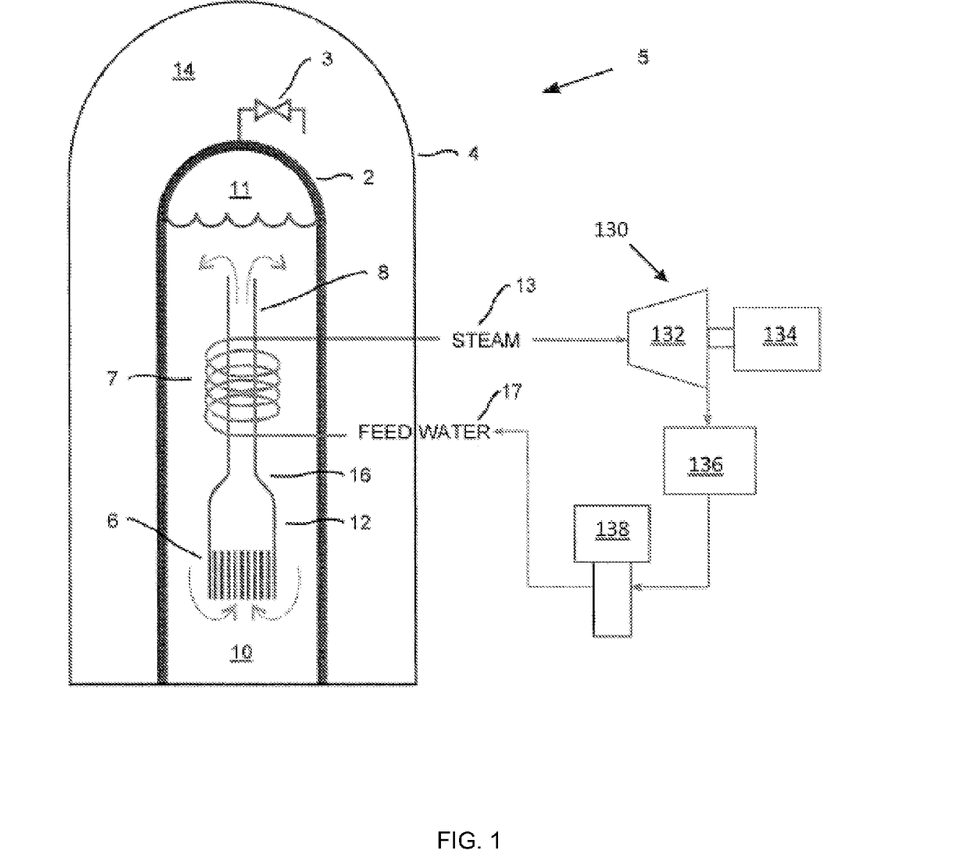
FIG. 1 is a block diagram illustrating a nuclear reactor system with a steam generator.

FIG. 1 illustrates an example nuclear power system 5 including a secondary cooling system 130. The secondary cooling system 130 includes or is fluidly coupled to a steam generator 7 that provides a heat transfer pathway for a feedwater 17 to receive heat from a primary coolant 10 in the nuclear power system 5. The steam generator 7, in some aspects, may include a plurality of tubulars (e.g., metallic or other tubulars or conduits) that may include one or more bends or turns. In some aspects, the steam generator 7 can be tested, for example, by the steam generator probe system shown in FIG. 4A, to ensure the integrity and safety of the tubulars. In some aspects, for example, the tubulars may be tested by a steam generator probe, such as that shown in FIG. 3, that is part of the steam generator probe system.

In the illustrated implementation, a reactor core 6 is surrounded by a reactor vessel 2. Primary coolant 10, such as water or sodium, in the reactor vessel 2 surrounds the reactor core 6. The reactor core 6 is further located in a shroud 12 which surrounds the reactor core 6 about its sides.

When the primary coolant 10 is heated by the reactor core 6 as a result of fission events, the primary coolant 10 is directed from the shroud 12 and out of a riser 8. This results in further primary coolant 10 being drawn into and heated by the reactor core 6 which draws yet more primary coolant 10 into the shroud 12. The water 10 that is transmitted through the riser 8 is cooled down by a heat exchanger or steam generator 7 and directed towards the annulus 16 and then returns to the bottom of the reactor vessel 2 through natural circulation.

The reactor vessel 2 is surrounded by a containment vessel 4. The containment vessel 4 is designed so that water or steam from the reactor vessel 2 is not allowed to escape into the surrounding environment. Pressurized steam 11 may be produced with heaters in the reactor vessel 2 as a means to maintain and to control the pressure in the reactor vessel. Water spray may be used in the top of the reactor vessel as an additional means to maintain and to control the pressure in the reactor vessel. A steam valve 3 is provided to vent steam 11 from the reactor vessel 2 into the containment vessel 4. In one implementation, the reactor vessel 2 is surrounded in a partial vacuum. The partial vacuum outside the reactor vessel in the containment space may be used to reduce the presence of flammable gasses in the containment space and to produce an insulating space for the reactor vessel.

The steam generator 7 circulates feedwater 17 and steam 13 in the secondary cooling system 130 in order to generate electricity with a turbine 132 and generator 134. The feedwater 17 passes through the steam generator 7 where it is boiled to steam and the steam becomes superheated. The secondary cooling system 130 may include a condenser 136 and optional feedwater pump 138. The steam 13 and feedwater 17 in the secondary cooling system 130 are isolated from the primary coolant in the reactor vessel 2, such that they are not allowed to mix or come into direct contact with each other. The primary coolant 10 circulates through the reactor vessel 2 as a result of temperature and pressure differentials that develop as a result of heat generation through reactor operation and through heat exchange with the secondary cooling system 130. Accordingly, the efficiency of the circulation depends on the thermal properties of the reactor module 5 as well as its physical design and geometry.

Figure 2A:
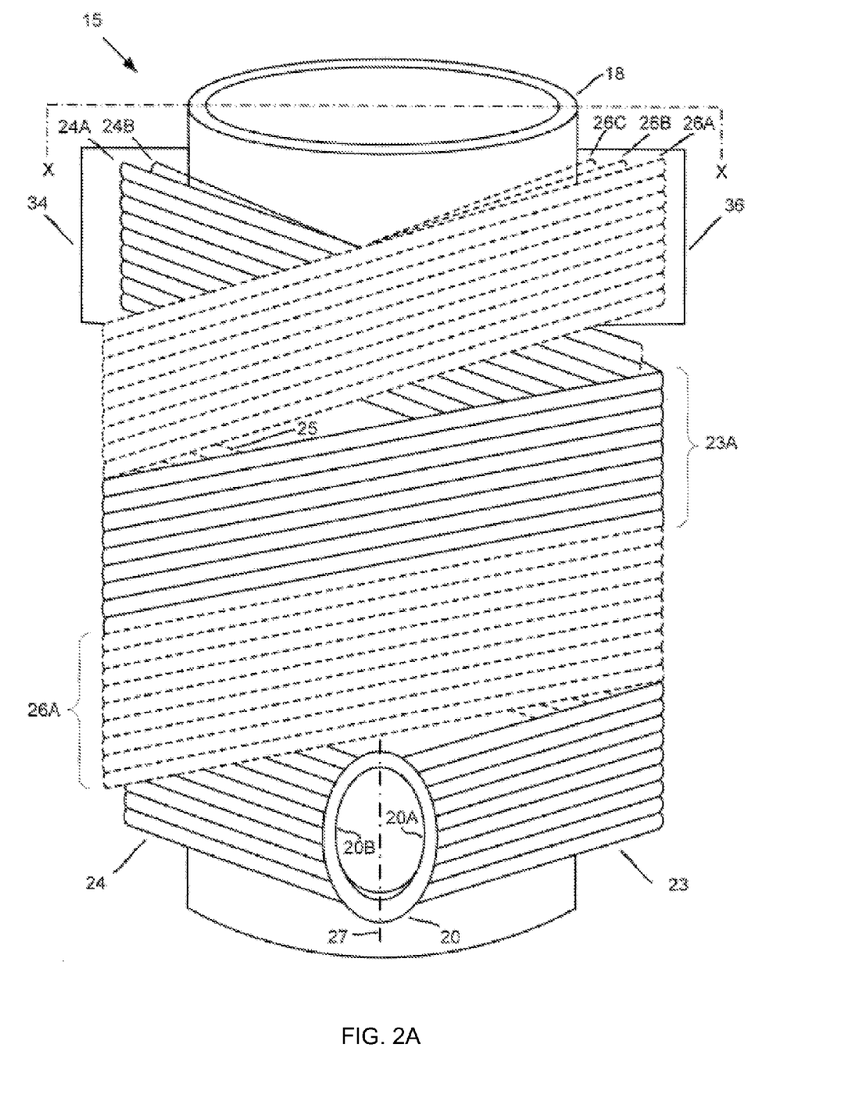
FIGS. 2A-2B illustrate an example steam generator that includes a plurality of heat transfer tubes.

FIG. 2A illustrates an example steam generator 15 comprising a plurality of heat transfer tubes. In some implementations, the steam generator 15 may be a helical coil steam generator, in which one or more tubes of the steam generator may be wound to form a serpentine or helical fluid pathway for a working fluid (e.g., water or other fluid) to circulate therethrough. Steam generator 15 is an example of a specific type and design of a helical coil steam generator that can be tested by, for example, the steam generator probe system shown in FIG. 4A and/or the steam generator probe shown in FIG. 3. However, the present disclosure contemplates that the steam generator probe system shown in FIG. 4A and/or the steam generator probe shown in FIG. 3 can test other types or designs of steam generators besides the helical coil steam generator shown in FIGS. 2A-2B.

The steam generator 15, in some aspects, may be used as the steam generator 7 and may include one or more steam generators, or bundles, comprising a lower integral tubesheets/plenums ("ITP") 20 configured to receive feedwater, and one or more upper ITPs 34, 36 configured to transport steam away from the reactor core, for example, to a turbine such as in the secondary cooling system 130 of FIG. 1. The lower ITP 20 and upper ITPs 34, 36 are shown mounted to a thermal housing 18. In one implementation, the housing 18 comprises the riser 8 and/or annulus 16 of FIG. 1 through which the primary coolant 10 circulates past the reactor core 6. The integral steam generator and steam generator 15 may be located within a pressure vessel, such as reactor vessel 2 or containment vessel 4 of FIG. 1.

The lower ITP 20 is illustrated as including a first side 20A and a second side 20B. In one implementation, first side 20A is a first tube sheet, whereas second side 20B is a second tube sheet. The lower ITP 20 is further illustrated as having an arcuate, circular, or elliptical shape. The lower ITP 20 includes a major axis 27 oriented in a vertical direction, wherein the first and second sides 20A and 20B are located on opposite sides of the axis 27. The one or more tubes sheets 20A, 20B may form an elliptical ITP 20. The first and second tube sets 23, 24 may be fluidly coupled to the elliptical ITP 20 on opposite sides of the major axis 27. A second lower ITP (not shown) may be included on a second and opposite side of the housing 18 as the lower ITP 20. Similarly, the second lower ITP may also include first and second sides as described above.

A first set of heat transfer tubes 23 is fluidly coupled to the first side 20A of the lower ITP 20. In one implementation, the first set of heat transfer tubes 23 includes a plurality of tubes fluidly coupled to a plurality of stubs protruding from the first side 20A. The first set of heat transfer tubes 23 is shown coiled around the housing 18 in a substantially clockwise direction. For simplicity of illustration, the number of times the first set of heat transfer tubes 23 coils around the housing 18 is shown as being approximately one and three quarters, whereas in practice the number of coils may include several or any number of revolutions corresponding to the length, rotational diameter, and helical angle of the tubes.

A second set of heat transfer tubes 24 is fluidly coupled to the second side 20B of the lower ITP 20 opposite the first set of heat transfer tubes 23. In one implementation, the second set of heat transfer tubes 24 includes a plurality of tubes fluidly coupled to a plurality of stubs protruding from the second side 20B. The second set of heat transfer tubes 24 is shown coiled around the housing 18 in a substantially counter-clockwise direction. For simplicity of illustration, the number of times the second set of heat transfer tubes 24 coils around the housing 18 is shown as being approximately one and one quarter, although other implementations include fewer or more revolutions.

In one implementation, the number of revolutions of the coils is between three and one quarter, and four and three quarters. Other implementations may include fewer or more revolutions of the coils. The direction of rotation of the sets of coils may be in a different or opposite rotational sense.

The plurality of tubes may be formed using varying numbers or rotations about the central axis to minimize the variation in the lengths of the tubes as the location of the tubes transitions from inside columns to outside columns. The paths of the tubes may also be adjusted to help minimize the variations in the lengths of the tubes. The helical angles of the heat transfer tubes may vary to account for the different radial locations of the corresponding coils. In some aspects, having tubes of substantially equal length promotes a constant pressure drop and equal fluid flow through each tube/set.

Whereas the lower ITP 20 is shown attached to a lower end of the housing 18, the upper ITPs 34, 36 are shown attached to an upper end of the housing 18. The second lower ITP (see FIG. 2B, ref. 28) is also attached to the lower end of the housing 18. Heat exchange tubes connected to the second lower ITP are illustrated in FIG. 2A using dashed lines to distinguish from the heat exchange tubes shown in solid lines that are associated with the first bundle of heat transfer tubes 23, 24 connected to the lower ITP 20.

In one implementation, the heat transfer tubes 23, 24 associated with the first lower ITP form a first steam generator bundle, whereas the heat transfer tubes 25, 26 associated with the second lower ITP 28 (FIG. 2B) form a second steam generator bundle. A given steam generator bundle may comprise additional sets of heat transfer tubes, for example heat transfer tubes 25 or heat transfer tubes 26. In one implementation, the additional sets of heat transfer tubes are connected to the ITP 28 (FIG. 2B) on opposite sides of tube sheets, similar to that discussed for the connection of the heat transfer tubes to lower ITP 20.

Heat transfer tubes 24A and 24B (collectively heat transfer tubes 24) are shown connected to the same side of the upper ITP 34. Heat transfer tubes 26A, 26B, and 26C (collectively heat transfer tubes 26) are shown connected to the same side of upper ITP 36. The first set of heat transfer tubes 23 may be understood as connecting to an opposite side of the upper ITP 34 as the second set of heat transfer tubes 24. Similarly, a third set of heat transfer tubes 25 may be understood as connecting to an opposite side of the upper ITP 36 as a fourth set of heat transfer tubes 26.

The lower ITP 20 is fluidly coupled to the first and second sets of heat transfer tubes 30 23, 24. Secondary coolant or feedwater entering the lower ITP is converted to steam in the first and second sets of heat transfer tubes 23, 24. The one or more upper ITPs 34, 36 are configured to transport the steam away from the steam generator. The first set of heat transfer tubes 23 cross over the second set of heat transfer tubes 24 at an elevation between the lower ITP 20 and the upper ITP 36. The first upper ITP 34 may be fluidly coupled to both the first set of heat transfer tubes 23 and the second set of heat transfer tubes 24. The first set of heat transfer tubes 23 may be connected to the first upper ITP 34 on an opposite side from that of the second set of heat transfer tubes 24. The second upper ITP 36 may be fluidly coupled to both the third set of heat transfer tubes 25 and the fourth set of heat 5 transfer tubes 26. In one implementation, the first upper ITP 34 is located on an opposite side of the steam generator as the second upper ITP 36. The second lower ITP 28 (FIG. 2B) may be fluidly coupled to the second upper ITP 36 via both the third set of heat transfer tubes 25 and the fourth set of heat transfer tubes 26.

Primary coolant that passes through the reactor core 6 (FIG. 1) and up through the inside of housing 18 circulates back down around the outside of housing 18, similar to that described with respect to FIG. 1, and past the heat transfer tubes 23, 24, 25, 26. By nature of the crisscross arrangement of heat transfer tubes, the flow of primary coolant by and between the heat transfer tubes 23, 24, 25, 26 cascades past the alternating tubes to ensure consistent and even flow rates through the steam generator 15. The flow of primary coolant causes the secondary coolant flowing through the heat transfer tubes 23, 24, 25, 26, to heat up and turn to steam, as discussed above. By coiling the heat transfer tubes it is possible to increase a surface area of the tubes for a given axial cylinder in order to maximize the heat transfer from the primary coolant to the secondary coolant.

Figure 2B:
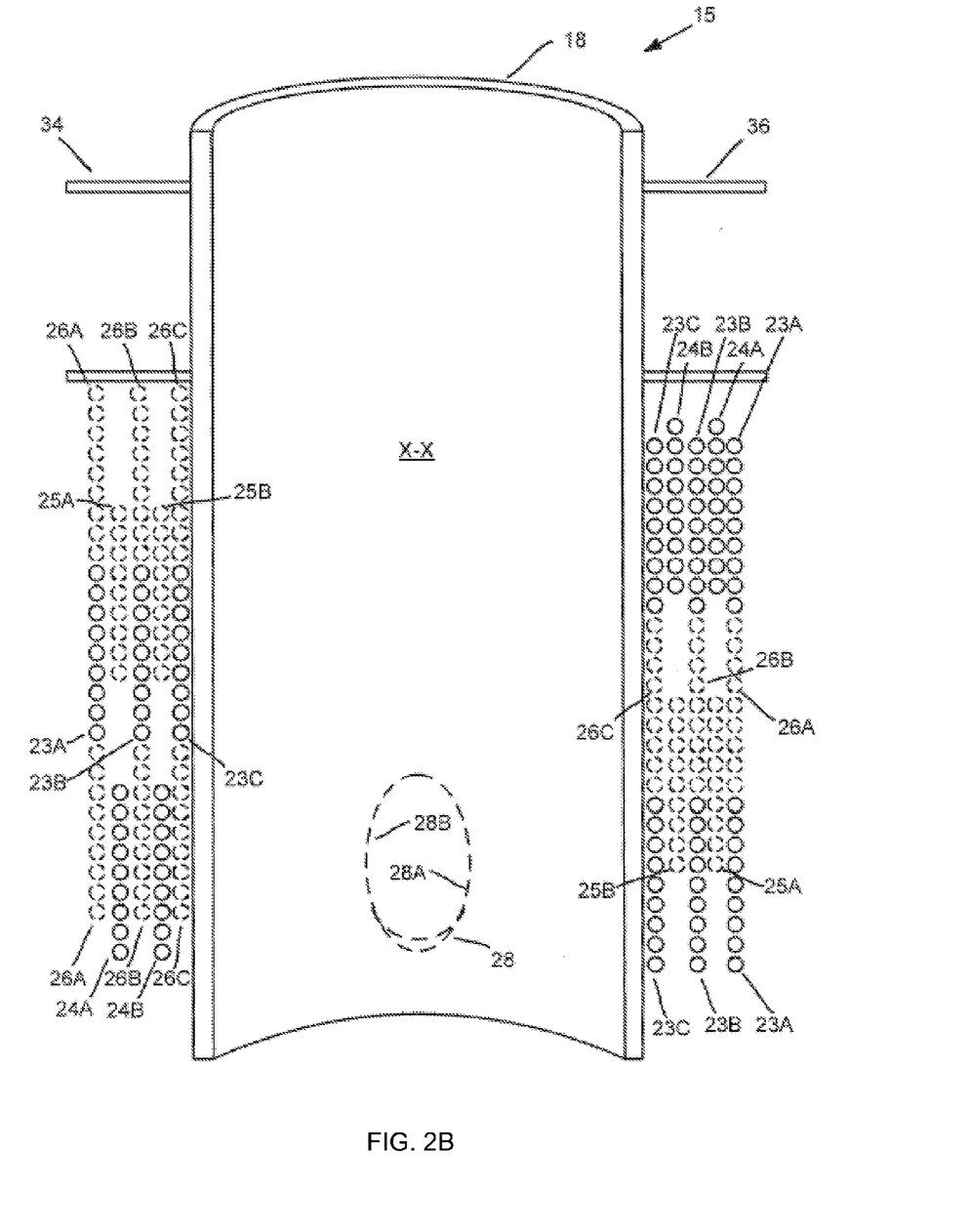

The first set of heat transfer tubes 23 is illustrated as including a row of heat transfer tubes 23A on the outside layer of the steam generator. Similarly, the fourth set of heat transfer tubes 26 is illustrated as including a row of heat transfer tubes 26A on the outside layer. The second and third sets of heat transfer tubes 24, 25 may be understood to have corresponding rows of heat transfer tubes which coil about the housing 18 in an opposite direction from rows 23A, and 26A. The rows of heat transfer tubes 23A, 26A may be understood to form the outside layer of the steam generator 15, whereas a next, inner layer of the steam generator 15 may be understood to be formed by corresponding rows of the second and third sets of heat transfer tubes 24A, 25A (FIG. 2B). In one implementation, the rows of heat transfer tubes 23A, 26A form adjacent rows of coils that rotate about the housing 18 in the same direction.

The elliptical shape of the ITP 20 allows for both horizontal and vertical attachment of the heat transfer tubes 23, 24. Orienting the ITP 20 in a substantially vertical direction allows for minimum wall thickness, and provides a hydrodynamic shape which minimizes pressure loss across the steam generator and reduces the cross section and impedance to the flow of primary coolant within the reactor vessel. Whereas the upper and lower ITPs are generally described as being oriented in a vertical direction, other implementations include orienting the ITPs in a substantially horizontal direction.

The initial section of the tube sets 23, 24 may be connected to the lower ITP 20 at a steeper angle than intermediate portions of the coils, in order to provide sufficient clearance over the lower ITP(s). The tube sets 23, 24 may also include a portion having a relatively shallower angle to offset the steeper angled portion to reduce the differences between helical angles of the various coils.

FIG. 2B illustrates a cross-section x-x taken through the steam generator 15 of FIG. 2A. Upper ITPs 34, 36 are illustrated as being connected to the housing 18 on opposite sides. Lower ITP 28 is illustrated with dashed lines as being connected on the back side of the housing 18, and as including first and second sides 28A and 28B, similar to that described above with respect to the first and second sides 20A, 20B of lower ITP 20.

Heat transfer tubes 23, 24 which originate in the lower ITP 20 (FIG. 2A) are shown as solid circles, whereas the heat transfer tubes 25, 26 which originate in the lower ITP 28 are shown as dashed circles for purposes of clarity only. The cross-section x-x is intended to illustrate the crisscross nature of the varying layers or rows of heat transfer tubes that are coiled about the housing. For example, the first, inner-most, layer is shown as including heat transfer tubes 23C, 26C. The second layer is shown as including heat transfer tubes 24B, 25B. The third layer is shown as including heat transfer tubes 23B, 26B. The fourth layer is shown as including heat transfer tubes 24A, 25A. The outer layer is shown as including heat transfer tubes 23A, 26A. Of course, there may be fewer or more layers of heat transfer tubes than that shown in the illustration. In one implementation, the heat transfer tubes comprise coils having alternating directions of rotation that cross over each other in coupling the lower ITP(s) 20, 28 to the upper ITP(s) 34, 36, respectively. For example, heat transfer tubes 26 alternately crisscross or cross over heat transfer tubes 25 in the following pattern: 26A, 25A, 26B, 25B, and finally 26C.

Whereas certain implementations illustrated thus far have described two lower ITP and two upper ITP, other implementations may include fewer or more lower and upper ITPs, and accordingly fewer or more sets of tubes or steam generators. In addition to maximizing the surface area for a given confined space, configuring the tubes as coils also causes liquid to be thrown to the outside of the tubes and therefore into closer proximity to the surrounding superheated primary coolant which therefore promotes more efficient conversion of the feed water into steam.

Figure 3:
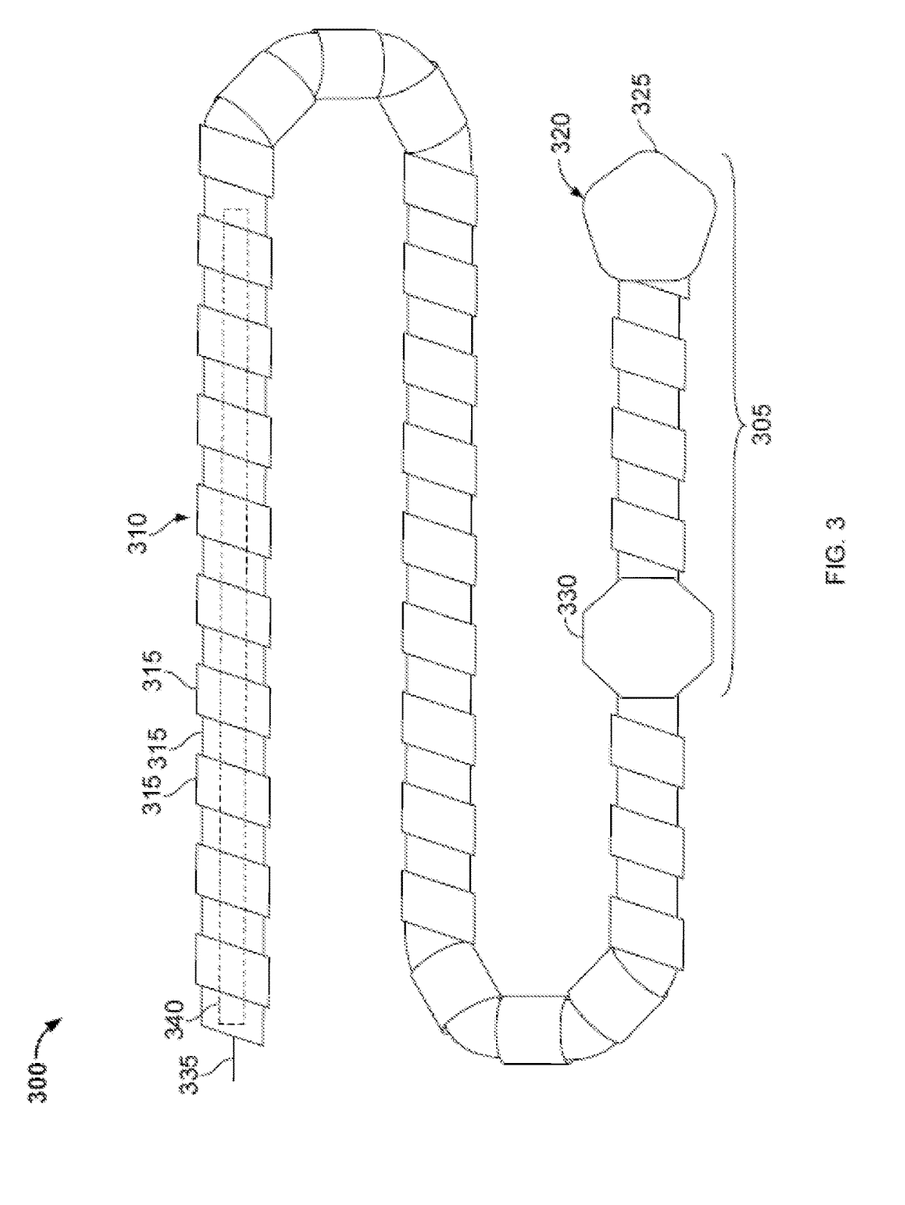
FIG. 3 illustrates an example implementation of a steam generator probe.

FIG. 3 illustrates an example implementation of a steam generator probe 300 that, in some implementations, may be used to test (e.g., eddy current test) one or more steam generator tubes, such as, for example, the heat transfer tubes 23 through 26 shown in FIG. 2. Of course, the steam generator probe 300 may be used to test other heat transfer tubes of non-helical type steam generators. In some aspects, the probe 300 may be designed (e.g., by length, diameter, and otherwise) to navigate an entire length of every tube of a steam generator, including U-bends, radiused portions, helical tubes, and straight portions of the tube. For example, steam generator tubes may include varying radius U-bends, a combination of square bends and varying radius U-bends, as well as straight (e.g., "once through") tubes.

As illustrated, the steam generator probe 300 includes a probe head 305 that is coupled (e.g., integrally, detachably, or permanently) to a flexible probe shaft 310. The illustrated probe head 305 includes a probe tip 320 that is coupled to an electronic probe 330 by a portion of the flexible conduit. In some aspects, the probe tip 320 includes a pointed, or rounded, portion 325 that helps facilitate entry of the probe head 305 into a steam generator tube for inspection and/or testing. For example, in some implementations, the pointed portion 325 may be bullet shaped to facilitate entry into the tube, as well as, in some aspects navigation of one or more bends in the tube.

The electronic probe 330 may be, in some aspects, a self-referencing, or differential, Bobbin coil probe. Other types of probes are contemplated as well, such as, for example, or other type of eddy current coils such as pancake coils or plus point coils, or even motorized rotating coils, and multi-coil arrays which generate directional currents in order to better detect flaws in a steam generator tube. For example, flaws may be manifested in several ways. For example, a particular flaw in a steam generator tube may include multiple or single axial and circumferential cracks on a primary and/or secondary side of the tubes, usually at support or top-of-tube sheet interfaces. As another example, a flaw may include fretting, such as wear at the Avanti-vibration bars and/or tube supports caused by tube vibration during operation. As yet another example, a flaw may include tube-to-tube wear. Thus, the type of electronic probe 330 may be based on the type of tube, the potential flaw type, or both, or other criteria.

The probe shaft 310 is constructed of a flexible conduit, such as a flexible metallic conduit, that is composed of multiple interlocking (e.g., telescoping) portions (e.g., rings) 315. In some aspects, the flexibility of the probe shaft 310 may be largely based on a degree of freedom, or movement, of each interlocking portion 315 relative to adjacent interlocking portions 315. The interlocking portions 315 may permit bending of the probe shaft 310 to facilitate movement of the steam generator probe 300 through bends, helical tubes, or other non-straight portions of a steam generator tube. Further, in some aspects, construction and/or material of the probe shaft 310 may be tailored (e.g., by adjusting flexibility, bending, axial & radial stiffness, offset, or otherwise) to a particular application (e.g., a particular type and/or shape of steam generator tube).

In some aspects, the probe shaft 310 is composed of stainless steel square-lock conduit (e.g., ⅜" or other size, depending on the steam generator tube diameter and other criteria). For example, the probe shaft 310 may be composed of stainless steel (e.g., 304, 316, or 400 series stainless steel) or other material, such as brass. In any event, the probe shaft 310 may be rust and corrosion resistant, with an internal diameter range of 0.375 to 0.400 inches, an external diameter range of 0.500 to 0.530 inches, and a bending radius of 1¾ inches. Other flexible conduits, or other square-lock conduit with different characteristics/dimensions, are also contemplated by the present disclosure for the probe shaft 310. For example, the probe shaft 315 may be Nylaflow® poly tubing or extruded poly shaft, as two examples. Other examples of materials and/or dimensions of the probe shaft 310 are within the scope of the present disclosure.

In some aspects, an exterior or outer surface of the probe shaft 310 may include extruded beads (or other raised surfaces) along the shaft 310 (e.g., at multiple intervals) to reduce contact area of the shaft 310 with an inner surface of a steam generator tube. For example, in some aspects, only the beads or other raised surfaces contact the inner surface of the tubing, thereby reducing the surface area and by extension, a friction between the shaft 310 and tubing.

In the illustrated implementation of the probe 300, a core 340 (shown in a dashed line) extends through at least a portion of the interior volume of the probe shaft 315 and/or probe head 305. In some implementations, the core 340 may extend through only a portion of the probe 300; in other implementations, the core 340 may extend through all or most of the probe 300. Further, in some implementations, the probe 300 may not include the core 340.

The core 340 may be composed of a wire (e.g., metallic or non-metallic) or braided wire (e.g., metallic or non-metallic) that provides axial strength and/or rigidity to the probe 300. For example, in some implementations, the core 340 may ease insertion of the probe 300 into and/or through a steam generator tube. Further, the core 340 may also provide and/or adjust the strength and/or rigidity of the probe shaft 310 as well.

The illustrated probe 300 also includes a communication line 335 that extends through the probe shaft 315 and is coupled to the electronic probe 330. The communication line 335 provides a communication path (e.g., for electronic or electrical signals, analog or digital signals, or otherwise) between the electronic probe 330 and, for instance, a control system (e.g., computer, microprocessor-based controller, laptop, tablet, smartphone, or other control system). For example, as an eddy current probe, the electronic probe 330 may measure a displacement of one surface (e.g., an interior surface of the steam generator tube) relative to the tip of the probe. A coil located in the tip of the probe 330 is energized to produce an electrical field around the tip of the probe 330. When a conductive surface (e.g., the interior surface of the steam generator tube) is placed in the field and the distance from the probe 330 is recorded, variations in this gap can be determined by the variations in the voltage flow to the probe 330. Such variations can then be transmitted through the communication line 335 to the control system for analysis.

Figure 4A:
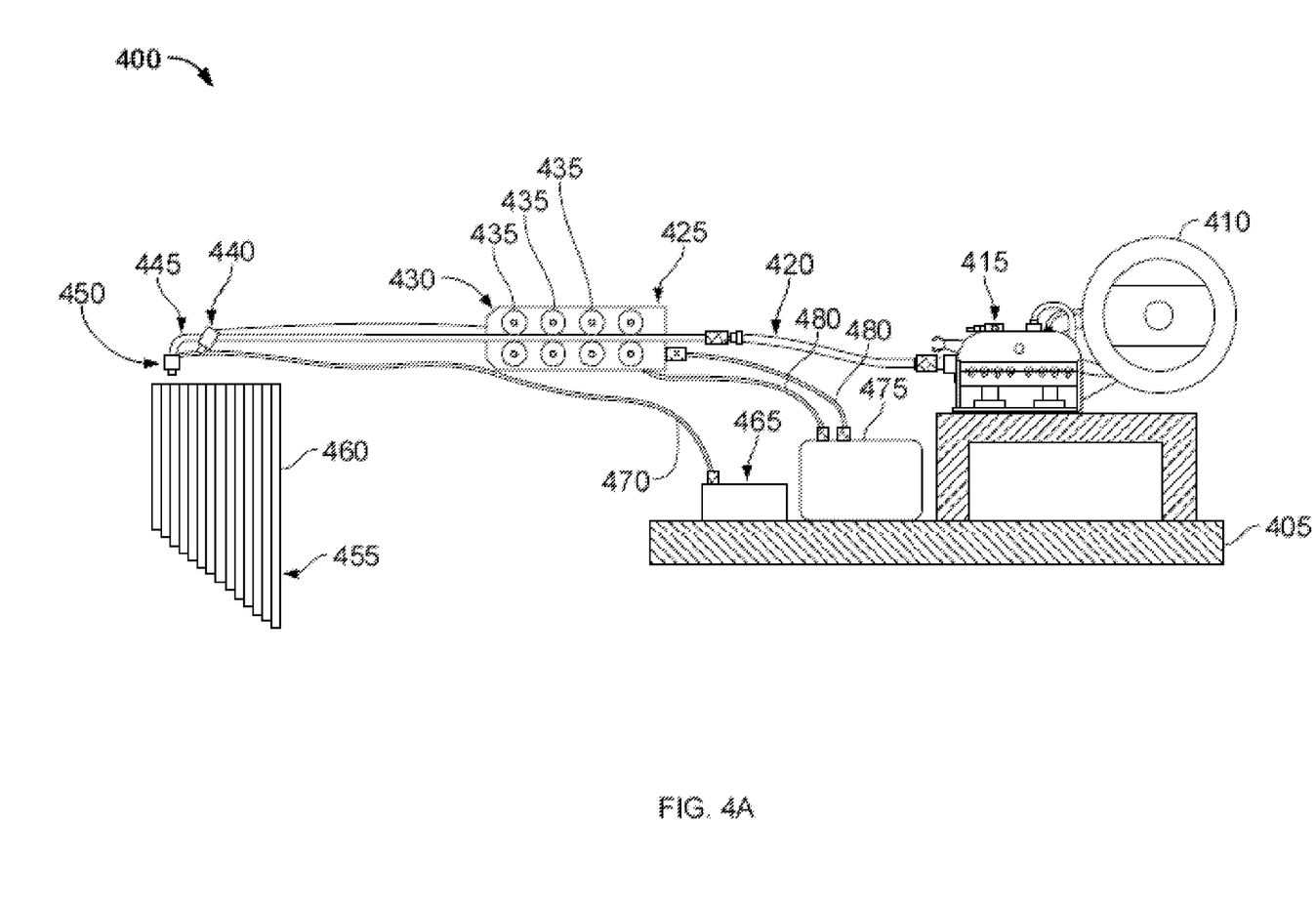
FIG. 4A illustrates an example implementation of a steam generator probe system.

FIG. 4A illustrates an example implementation of a steam generator probe system 400. In some implementations, the system 400 includes a probe pusher 415, a power module 475, and a pressurized gas supply 465 mounted on a support 405. The system 400 further includes a guide tube positioner 430 that includes one or more sets of rollers 435 (e.g., four sets are shown) that receive a steam generator probe 420 and position or help position the steam generator probe 420 for entry into a particular steam generator tube 460 of a steam generator 455 (a portion of which is shown in FIG. 4A).

The steam generator probe system 400 also includes, as illustrated, a spool 410 that may carry (e.g., in a continuous coil) a length of a flexible probe shaft that is part of the steam generator probe 420 (e.g., the probe shaft 315 shown in FIG. 3). The probe pusher 415 may receive the steam generator probe 420 from the spool 410 and convey the probe 420 towards, into and/or through the steam generator tube 460. For example, in some implementations, the probe pusher 420 may include a track drive that applies a force to the steam generator probe 420 to urge the probe 420 towards, into and/or through the guide tube positioner 430 and then the steam generator tube 460. Example implementations of the probe pusher 415 may include, for example, a CoreStar OMNI-200 TIP, a Zetec 3D, a Zetec Dual 10D, a Zetec MIZ80iD TIP, a R/D Tech TTS Rotating Probe Drive System, or a Inetec integrated probe positioning and pushing system. Other types of probe pushers 415 are also contemplated by the present disclosure. The probe pusher 415 may operate on 120 VAC 50/60 Hz power, and convey the steam generator probe 520 at a speed between 0.1 and 100 inches/second with a proportional control take-up spool.

The guide tube positioner 430 includes motorized or free spinning rollers 435 that receive the steam generator probe 420 therethrough and guide (all or partially) the probe 420 toward the steam generator tube 460. In some implementations, the guide tube positioner may provide for translation of the steam generator tube probe 420 in at least four directions (e.g., side-to-side and up-down) so as to position the probe 420 to enter the steam generator tube 460.

Figure 4B:
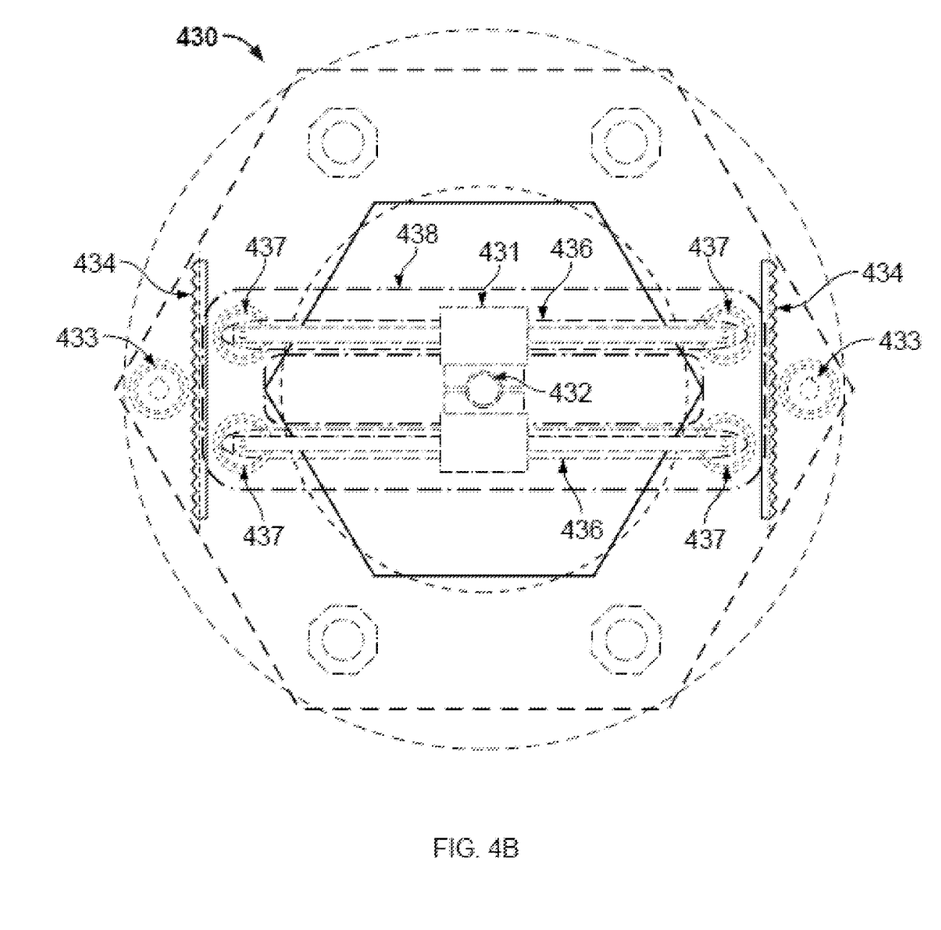
FIG. 4B illustrates a front view of an example implementation of a guide tube positioner that may be used in a steam generator probe system.

Turning to FIG. 4B, for instance, a front view of the guide tube positioner 430 is illustrated. As illustrated, the guide tube positioner 430 includes an aperture 434 in a guide tube trolley 431 that can receive the steam generator probe 420 therethrough. The trolley 431 is mounted on a support plate 438 that is moveable in two vertical directions (e.g., vertically up and vertically down) on tracks 434 that are engaged with drive gears 433 (e.g., on either side of the plate 438. Translation of the plate 438 on the tracks 434 may also translate the trolley 431 in a particular vertical direction. Further, the trolley 431 is translatable in two horizontal directions on continuous surfaces 436 (e.g., belts or chains) that are driven by drive gears 437 (e.g., gears or sprockets). Thus the steam generator probe 420 may be translated in multiple directions as it extends through the aperture 432. In some aspects, the steam generator probe 420 may also be radially translated (e.g., adjusted about a rotational axis or axes), such as, when a tubesheet or access requires such translation. In some aspects, rotation of the entire positioning system 430 may occur or just rotation of the plate 438.

Returning to FIG. 4A, the power module 475 may be electrically coupled (by power lines 48) to the guide tube positioner 430 to provide power to, for example, the drive gears 433 and 437. The power module 475 may also provide power to the probe pusher 415. In some implementations, the power module 475 may be a stand-alone and/or independent source of power (e.g., a battery, generator, or other source). However, the power module 475 may also be an electrical utility grid or other source. Further, although described as capable of providing electrical power to other components in the system 400, such components may be pneumatically powered, solar powered, hydraulically powered, or otherwise, by the power module 475.

In some implementations, the power module 475 may also include control electronics, such as hardware, software, and/or middleware that is executable to control all or a portion of the system 400. For example, the power module 475 may include a processor-based control system that includes digital electronic circuitry, or computer software, firmware, or hardware, or combinations of one or more of them. For example, the power module 475 may include a microprocessor based controller (or control system) as well as an electro-mechanical based controller (or control system). Instructions and/or logic in the control system (e.g., to control one or more methods or processes associated with the system 400 can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated non-transitory signal, e.g., a machine-generated electrical, optical, or electromagnetic signal that is generated to encode information for transmission to suitable receiver apparatus for execution by a data processing apparatus.

The control system can include clients and servers and/or master and slave controllers. A client and server are generally remote from each other and typically interact through a communication network. The relationship of client and server arises by virtue of computer programs running on the respective computers and having a client-server relationship to each other. In some aspects, the control system represents a main controller (e.g., master) communicably coupled through communication elements (e.g., wired or wireless) with one or more of the illustrated components of the system 400.

Figure 5:
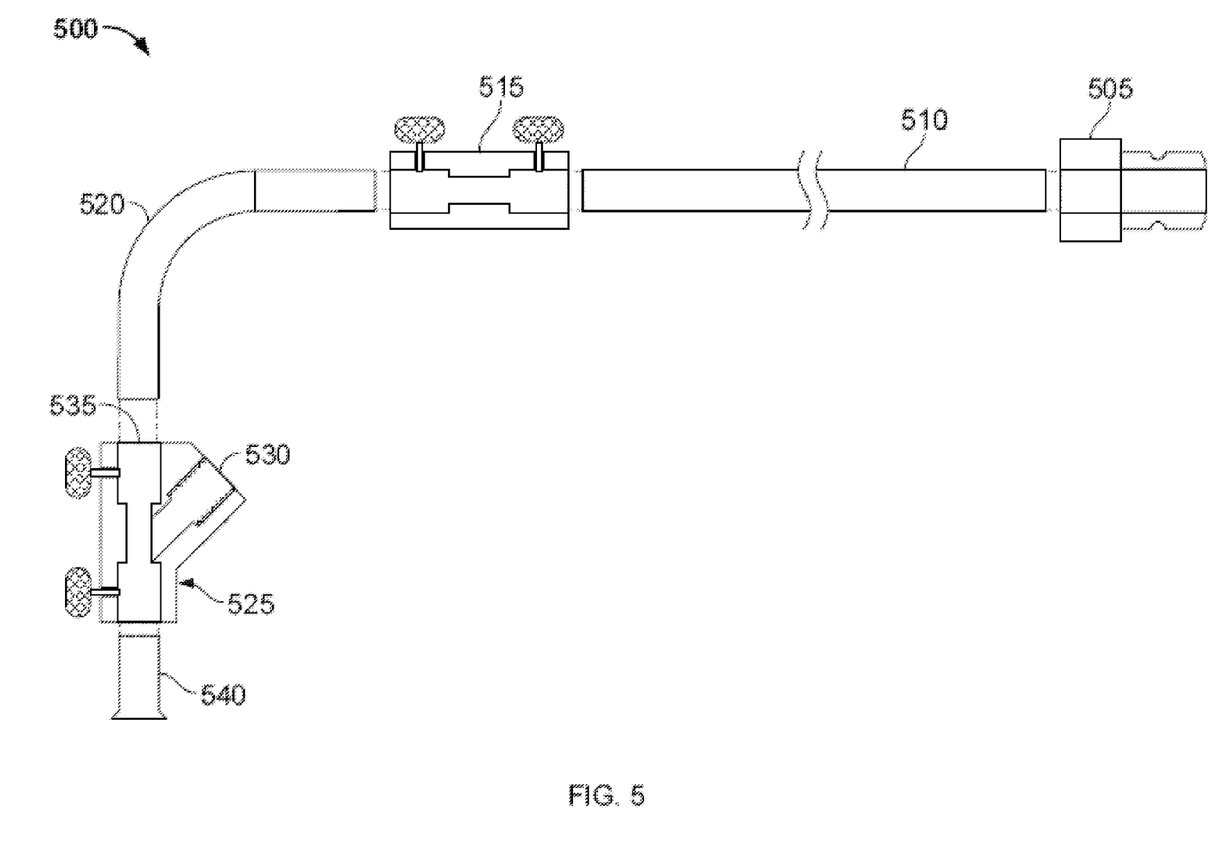
FIG. 5 illustrates an example implementation of a probe positioner for a steam generator probe.

As illustrated, the system 400 includes a camera 440 (e.g., still or motion) that is positioned on or near a probe positioner 445 (discussed more with reference to FIG. 5). The camera 440 may be communicably coupled to, for example, a control system of the power module 475 and may provide real-time or near-real time images (e.g., still and/or video) to a user of the control system to help position the steam generator probe 420 near an opening of the steam generator tube 460. With the assistance of such images, the user may more accurately manipulate a position of the steam generator probe 420 (e.g., with the guide tube positioner 430) to insert the steam generator probe 420 into the steam generator tube 460.

The illustrated pressurized gas supply 465 provides a flow of pressurized gas or fluid (e.g., air or other fluid) through a conduit 470 to a nozzle 450 positioned near or at an outlet of the probe positioner 445. In some implementations, a flow of pressurized gas (e.g., air) is provided substantially simultaneously with the steam generator probe 420 into and/or through the steam generator tube 460 during testing of the tube 460 with the probe 420 (as described in more detail below).

FIG. 5 illustrates an example implementation of a probe positioner 500 for a steam generator probe. In some aspects, the probe positioner 500 may be the same as or substantially similar to the probe positioner 445 shown in FIG. 4A. Generally, the illustrated probe positioner 500 may help facilitate entry of a steam generator probe (e.g., probe 300, probe 420, or otherwise) into and/or through a steam generator tube (e.g., tubes 23-26, tube 460, or otherwise) of a steam generator of a nuclear reactor system. In some aspects, the illustrated probe positioner 500 may be made with PVC conduit, metal conduit, or other tubular components. The probe positioner 500 may be integrated or coupled with, for example, a guide tube positioner, such as the positioner 430 shown in FIGS. 4A-4B.

As illustrated, the probe positioner 500 includes an inlet 505 that can be joined or connected to the guide tube positioner and can also be joined or connected (e.g., threadingly) to a tubular extension 510 (e.g., a variable length extension). The tubular extension 510, in turn, is coupled to a radius 520 through a coupling 515. The radius 520, in some aspects, may be variable or bendable so as to adjust through a range of degrees (e.g., between 60 and 120 degrees).

The radius 520 is coupled to a y-coupling 525 that includes a probe inlet 535 and a gas flow inlet 530. The y-coupling 525, therefore, can receive a steam generator probe into and/or through the probe inlet 535 while also receiving a flow of pressurized gas (e.g., air from a pressurized gas supply) into and/or through the gas flow inlet 530 and join the probe and flow of gas together to an outlet 540. The outlet 540 can be positioned near, at, and/or coupled to an inlet (or outlet) of a steam generator tube to allow the probe and flow of gas to enter into the steam generator tube.

Figure 6:
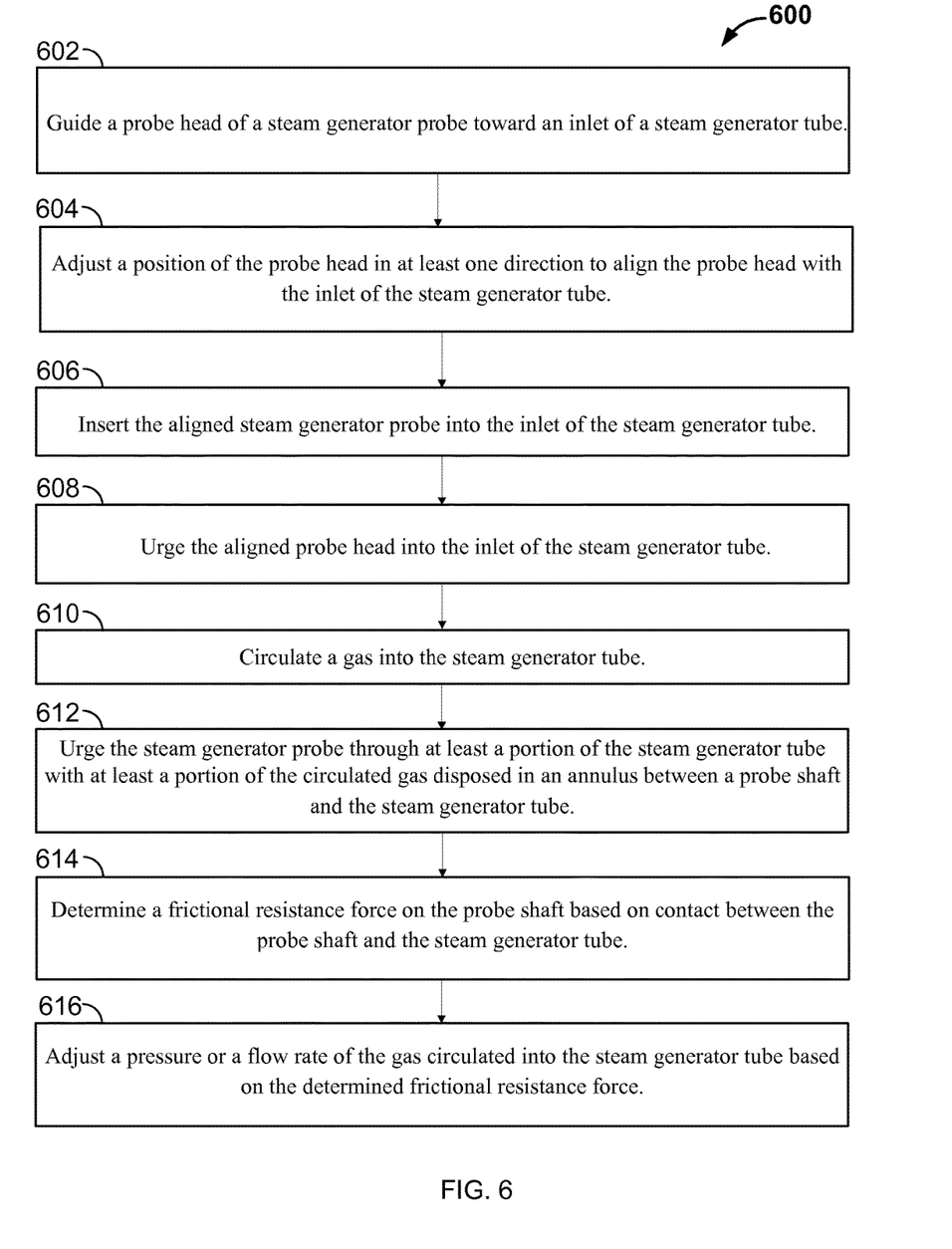
FIGS. 6-7 illustrate example methods for inspecting and/or testing a steam generator tube.

FIG. 6 illustrates an example method 600 for inspecting and/or testing a steam generator tube. In some aspects, method 600 may be performed using all or part of the steam generator probe system 400 (including the steam generator probe 420 or 300 or other probe), or another system for testing a steam generator tube with a steam generator probe.

Method 600 may begin at step 602, when a probe head (e.g., probe head 305) of a steam generator probe (e.g., probe 300) is guided toward an inlet of a steam generator tube. For example, in some aspects, a probe pusher (e.g., probe pusher 415) may urge the probe head (and rest of the steam generator probe) toward an inlet (or outlet) of the steam generator tube based on an automated or semi-automated control system or under user control of the probe pusher.

In step 604, a position of the probe head is adjusted in at least one direction to align the probe head with the inlet of the steam generator tube. In some aspects, for example, the position of the probe head may be adjusted with a guide tube positioner (e.g., guide tube positioner 430). For example, as described with reference to FIG. 4B, the guide tube positioner 430 may adjust a position of the steam generator probe (and probe head) vertically and/or horizontally to align the probe head with the inlet of the steam generator probe.

In step 606, the aligned steam generator probe is inserted into the inlet of the steam generator tube. In some aspects, the probe may be inserted into an inlet of the tube as defined by a flow direction of a working fluid through the tube (e.g., a "top down" insertion). In other aspects, the probe may be inserted into an outlet of the tube as defined by a flow direction of a working fluid through the tube (e.g., a "bottom up" insertion).

In step 608, the steam generator probe is urged through the inlet of the steam generator tube and, in some aspects, begins to be urged through the tube to test (e.g., eddy current test) the tube.

In step 610, a flow of a gas (e.g., air) is circulated into the steam generator tube. In step 612, the steam generator probe is urged through at least a portion of the steam generator tube with at least a portion of the circulated gas. For example, the flow of gas may be provided through the tube substantially simultaneously with step 608 so that both the probe and the flow of gas are provided through the steam generator tube at the same time. In some aspects, the flow of gas may circulate in an annulus between the steam generator probe and an interior surface of the steam generator tube. In some aspects, the circulated air may buffer or cushion the steam generator probe as it is urged through the steam generator tube, thereby reducing (all or partially) a frictional contact between the probe and the tube. For example, circulation of a gas flow (e.g., an airflow) into the tube around a probe shaft of the steam generator probe may help break up building friction and resultant drag as the probe is inserted and/or retracted through the steam generator tube.

In some aspects, step 612 may include inserting the steam generator probe into the steam generator tube to the desired location. Once the probe is located at the desired location, inspection data (e.g., eddy current data) can be recorded. Such inspection data may identify (all or partially) a presence and size of one or more defects in the tube during probe withdrawal from the tube.

In step 614, a frictional resistance force on the probe shaft (or other component) of the steam generator probe based on contact between the probe and steam generator tube may be determined. For example, in some aspects, an estimate of the frictional resistance force may be determined based on an amount of torque necessary to propel the steam generator probe by a probe pusher.

Other techniques for determining or estimating the frictional resistance force are also contemplated by the present disclosure. In some aspects, for example, a load cell may be used to calculate friction based on a force necessary to overcome such friction. In some aspects, a probe pusher may include a "traction control" system, which monitors an idler wheel encoder on the probe shaft and the load on the electric drive motor. If the drive load increases and the probe shaft does not move within a speed tolerance (e.g., set by a user), then a pinch pressure on the drive wheels is increased to avoid slipping. If the load on the drive motor exceeds a set threshold and the idler encoder shows that the probe shaft is not moving, then the system may stop (e.g., automatically) in order to avoid damage the probe shaft or rubber drive belt or wheels (e.g., depending on the probe pusher type).

In step 616, a pressure or flow rate of the gas circulated into the steam generator tube may be adjusted (e.g., automatically) based on the determined frictional resistance force encountered. In some aspects, as the determined or estimated force decreases, a pressure or flow rate of the gas (e.g., air) may also be reduced. As the determined or estimated force increases, the pressure or flow rate of the gas (e.g., air) may be increased to help urge the steam generator probe through the steam generator tube. As another example, the pressure or flow rate of the gas may be increased as the steam generator probe approaches certain portions of the steam generator tube, such as, for example, U-bends, helical portions, or other curved or radiused sections.

In some aspects, this adjustment may be performed through a feedback loop which monitors the electric load on the probe pusher drive motor and the encoded movement of the probe shaft. For example, control algorithms (e.g., in software, hardware, middleware, or a combination thereof) executed by a probe pusher may have automated sequence control that self-adjusts based on the position of the probe, e.g., either by a readout of the probe shaft idler wheel encoder or by detecting landmark signals in the data such as from tube support structures which are located at known positions.

Figure 7:
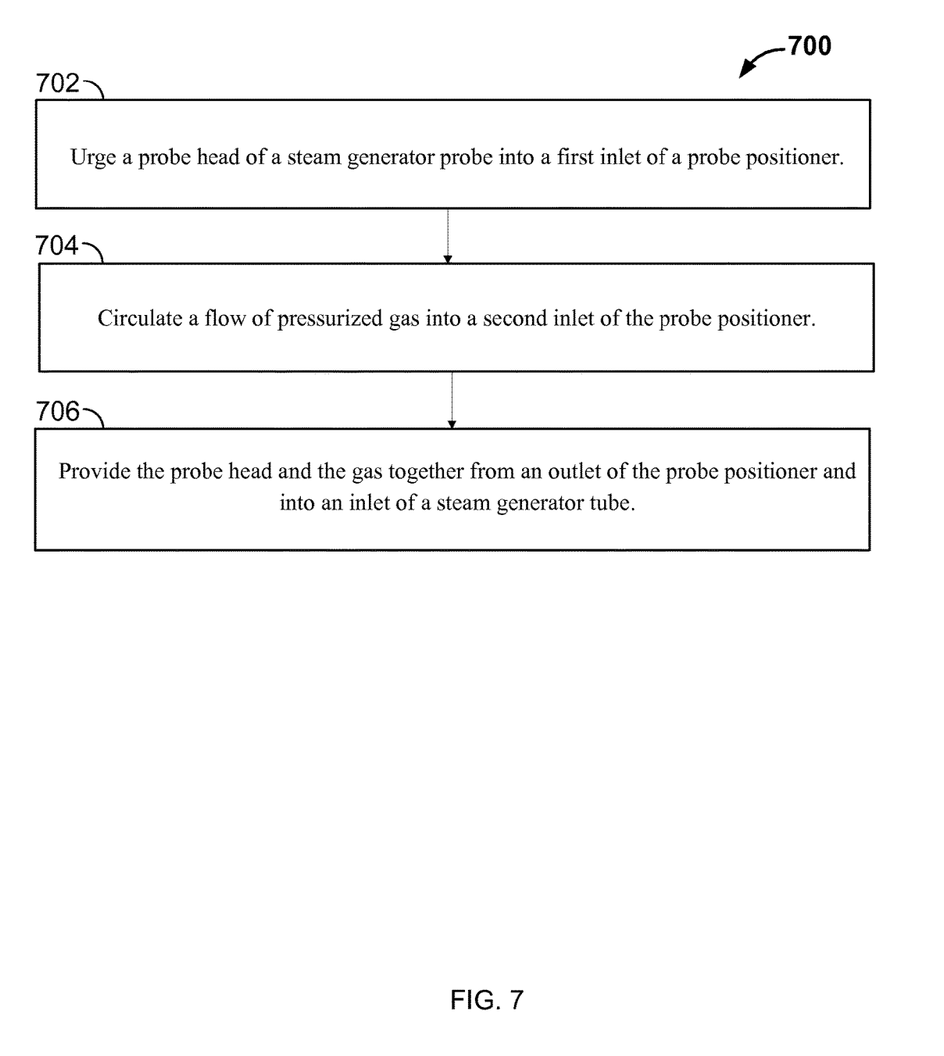

FIG. 7 illustrates an example method 700 for inspecting and/or testing a steam generator tube. In some aspects, method 700 may be performed using all or part of the steam generator probe system 400 (including the steam generator probe 420 or 300 or other probe, or another system for testing a steam generator tube with a steam generator probe, as well as the probe positioner 500 shown in FIG. 5. In some aspects, method 700 may be performed as part of method 600 (e.g., in between steps 604 and 606).

Method 700 may begin at step 702, when a probe head (e.g., probe head 305) of a steam generator probe (e.g., probe 300) is urged into a first inlet of a probe positioner. For example, as shown in FIG. 5, the probe head may be urged (e.g., by a probe pusher) into the inlet 505 of the example probe positioner 500. The probe head, and attached probe shaft, of the steam generator probe may be urged through the extension 510, coupling 515, radius 520 and into the y-coupling 525 (e.g., through inlet 535).

In step 704, a flow of pressurized gas (e.g., air) is circulated into a second inlet of the probe positioner. For example, as shown in FIG. 5, the pressurized gas may be circulated through inlet 530 of the y-coupling 525. The gas may be air, another gas, or another fluid such as water, oil, or other liquid.

In step 706, the probe head of the steam generator probe and the gas are provided from an outlet of the probe positioner and into an inlet of the steam generator tube. For example, as shown in FIG. 5, the probe and gas may be provided through the outlet 540 and into the steam generator tube. In some aspects, the steam generator probe may be inserted into the steam generator tube (through the probe positioner) without any flow of the gas. Subsequent to insertion of the steam generator probe into the tube, the flow of pressurized gas may be provided to the second inlet to join the steam generator probe into the steam generator tube.

Although the implementations provided herein have primarily described a pressurized water reactor, it should be apparent to one skilled in the art that the implementations may be applied to other types of power systems as described or with some obvious modification. For example, the implementations or variations thereof may also be made operable with a sodium liquid metal reactor, pebble-bed reactor, or a reactor designed to operate in space, such as in a propulsion system with limited operational space. Whereas certain implementations describe use of the helical coil steam generator in a nuclear reactor, the steam generator could also be made to operate with a conventional steam generating power facility. Similarly, the steam generators can be configured to operate with either natural or forced circulation.

A number of implementations have been described. Nevertheless, it will be understood that various modifications may be made. For example, advantageous results may be achieved if the steps of the disclosed techniques were performed in a different sequence, if one or more steps were added or replaced, if components in the disclosed systems were combined in a different manner, or if the components were replaced or supplemented by other components. Accordingly, other implementations are within the scope of the following claims.

What is claimed is:

1. A steam generator tube probe, comprising:
 a probe head comprising a probe tip at a proximal portion of the probe head, the probe tip being configured for entry into a steam generator tube, an electronic probe at a distal portion of the probe head, and a first flexible conduit coupling the probe tip to the electronic probe, the first flexible conduit comprising a first plurality of metallic interlocking portions, each interlocking portion from the first plurality of interlocking portions being moveably affixed to at least one adjacent interlocking portion from the first plurality of interlocking portions; and
 a probe shaft coupled to the distal portion of the probe head and comprising a second flexible conduit that comprises a second plurality of metallic interlocking portions, each interlocking portion from the second plurality of metallic interlocking portions being moveably affixed to at least one adjacent interlocking portion.

2. The steam generator tube probe of claim 1, further comprising:
 a cable that extends from at or adjacent the distal portion of the probe head through the probe shaft.

3. The steam generator tube probe of claim 2, wherein the cable comprises a multi-strand cable.

4. The steam generator tube probe of claim 1, wherein the flexible metallic conduit comprises a stainless steel squarelock conduit.

5. The steam generator tube probe of claim 1, wherein the electronic probe comprises an eddy current test probe.

6. The steam generator tube probe of claim 5, wherein the eddy current test probe comprises a self-referencing Bobbin coil probe.

7. A method of testing a steam generator tube, comprising:
 inserting a steam generator tube probe into an inlet of a helical steam generator tube, the steam generator tube probe comprising a probe head having a probe tip coupled to an electronic probe via a first flexible conduit, the first flexible conduit comprising a first plurality of metallic interlocking portions, each interlocking portion from the first plurality of interlocking portions being moveably affixed to at least one adjacent interlocking portion from the first plurality of interlocking portions, the electronic probe of the probe head further being coupled to a probe shaft that includes a second flexible metallic conduit comprising a plurality of interlocking portions; and
 urging the steam generator tube probe through at least a portion of the helical steam generator tube.

8. The method of claim 7, further comprising:
 circulating a flow of a gas through the helical steam generator tube substantially simultaneously with the urging of the steam generator tube probe through the portion of the helical steam generator tube.

* * * * *